United States Patent
Berry, III

(10) Patent No.: US 7,473,909 B2
(45) Date of Patent: Jan. 6, 2009

(54) USE OF ION INDUCED LUMINESCENCE (IIL) AS FEEDBACK CONTROL FOR ION IMPLANTATION

(75) Inventor: Ivan L. Berry, III, Amesbury, MA (US)

(73) Assignee: Axcelis Technologies, Inc., Beverly, MA (US)

( * ) Notice: Subject to any disclaimer, the term of this patent is extended or adjusted under 35 U.S.C. 154(b) by 241 days.

(21) Appl. No.: 11/633,694

(22) Filed: Dec. 4, 2006

(65) Prior Publication Data
US 2008/0128621 A1 Jun. 5, 2008

(51) Int. Cl.
*H01J 37/08* (2006.01)

(52) U.S. Cl. .................. 250/492.21; 250/398; 250/399; 250/400; 250/492.1; 250/492.2; 250/492.3

(58) Field of Classification Search ................. 250/398, 250/399, 400, 492.1, 492.2, 492.21, 492.3, 250/336.1, 361 R, 362, 363.01; 118/723 CB, 118/723 FI, 715; 204/192.11, 192.34, 298.04, 204/298.36; 216/62; 427/523, 526, 527, 427/905
See application file for complete search history.

(56) References Cited

U.S. PATENT DOCUMENTS 4,800,100 A * 1/1989 Herbots et al. .............. 427/527
6,933,511 B2 * 8/2005 Yang et al. .............. 250/492.21

OTHER PUBLICATIONS

"Ion Induced Luminescence of Silica Glasses and Optical Fibers", S. Nagata, K. Toh, B. Tsuchiya, N. Ohtsu and T. Shikama, Penetrating Radiation Systems and Applications, V, Proceedings of SPIE, vol. 5199 (SPIE, Bellingham, WA, 2003), pp. 132-139.

* cited by examiner

*Primary Examiner*—Jack I Berman
*Assistant Examiner*—Michael Maskell
(74) *Attorney, Agent, or Firm*—Eschweiler & Associates, LLC

(57) ABSTRACT

An ion implantation system utilizing detected ion induced luminescence as feedback control that comprises, a wafer, a spectrometer, a photodetector, an ion source generator, wherein the ion source generator is configured to implant the wafer with ions, and the photodetector is configured to detect ion induced luminescence both on and off the wafer.

30 Claims, 8 Drawing Sheets

USE OF ION INDUCED LUMINESCENCE (IIL) AS FEEDBACK CONTROL FOR ION IMPLANTATION

FIELD OF THE INVENTION

The present invention relates generally to ion implantation for semiconductor processing systems, and more specifically to a method for optimizing ion implantation of a semiconductor substrate by employing luminescence as feedback control.

BACKGROUND OF THE INVENTION

The semi-conductor industry employs ion implantation in the manufacture and processing of very large scale integration (VLSI) microprocessors. Ion implantation is a process by which dopants are added to a semiconductor wafer by impacting energized and accelerated charged atoms or molecules (positive or negative ions) against semiconductor substrates. One of the objectives of ion implantation is to introduce a desired atomic species uniformly into a target material, the semiconductor wafer.

Measuring and/or attaining precise dose uniformity over a wafer surface is typically accomplished by scanning a beam of ions across the wafer surface. To ensure the surface of the wafer is "painted" uniformly by the beam generally requires feedback control of beam current, beam scan dwell, and the like to ensure acceptable across wafer implanted dose uniformity. Directly measuring beam current, for example while the ion beam is directly on the wafer is nearly impossible by conventional means and only indirect beam current monitoring methods are practical.

A Faraday cup is typically used in an ion implantation system as an indirect beam current measurement method. The Faraday cup system is utilized, for example, to determine the ion beam current, wherein the metal "cup" intercepts and traps the ionic particles. Typically, when the ion beam traverses off of the wafer it is measured with the Faraday cup, which is placed in the path of the ion beam. The ion beam charged particles strike the cup transferring charges from the beam to the cup and the resultant charge can be converted to an equivalent current indicative of the number of ions striking the cup. In this way the implantation current that the wafer "sees" can be determined as the beam is scanned back and forth across the wafer and can be adjusted if necessary. However, there are several problems associated with employing the approach, discussed supra. Depending on how fast the system scans the wafer will determine the speed at which the beam can be monitored, for example in some systems this is approximately every ten to twenty milliseconds. Even though the ion beam is measured at the Faraday cups, it is not known what is actually taking place on the wafer surface.

During an electrical glitch, for example, the ion beam is interrupted for a given time (e.g., one microsecond) that if taking place while the ion beam is "on wafer" would go undetected using a Faraday cup system.

An additional issue is that there are often background gases in the chamber, and when the ion beam strikes the background gas molecules the molecules can pull the charge off of the ions, neutralizing them. Subsequently, the "ion" keeps moving but it no longer has a charge (becomes a "fast atom"). The Faraday cup which detects charge no longer responds to or recognizes the fast atom, even though that atom can be implanted in the wafer and can change the wafer properties.

In view of the above problems it would therefore be desirable to have a system and method which mitigates such issues. Thus, there exists a need for an improved system and method for determining dose uniformity in semiconductor implantation.

SUMMARY OF THE INVENTION

The present invention overcomes the limitations of the prior art. Consequently, the following presents a simplified summary of the invention in order to provide a basic understanding of some aspects of the invention. This summary is not an extensive overview of the invention. It is intended to neither identify key or critical elements of the invention nor delineate the scope of the invention. Its purpose is to present some concepts of the invention in a simplified form as a prelude to the more detailed description that is presented later.

The present invention is directed generally toward a system and method for optimizing ion dose uniformity, while performing ion implantation of substrates. It is well known that all surfaces luminescence (emit photons) upon impact with energetic ions. This invention makes use of the luminescence signal obtained when the ion beam is striking the wafer and/or scan arm as a feedback signal to control the ion beam parameters, such as dosage, pressure compensation, and the like. The optical response of the luminescence can be very fast, on the order of microseconds or less depending upon the materials. The invention makes use of the wafer as the target, as opposed to or in conjunction with Faraday cups, providing real time understanding of the ion beam and wafer interaction on the surface of the wafer.

Ion induced luminescence (IIL) is a well understood physical process, wherein the emitted wavelengths of ion induced luminescence signal comprises peak characteristics of the target material and the impinging ion beam. Scintillation detectors, commonly used in early electron microscopes, are based upon this luminescence principle. An aspect of the present invention is that it can also facilitate identifying material properties and/or material analysis of the wafer. The unique characteristics of the ion induced luminescence signal can provide useful information, which if interpreted properly, can offer the possibility to correct for implantation errors that occur with the current art implantation approaches. Wafers undergoing ion implantation can have multiple materials exposed to the ion beam, for example, silicon, photoresist, oxides, metals, and the like, but in terms of the size of the ion implantation beam, these wafers "look" uniform across the wafer surface. Depending on what material the ion beam strikes, the luminescence given off by each material will have its own characteristic identifying wavelength. This allows materials analysis to be carried out on the wafer surface, for example. According to another aspect of the present invention, the system can be sensitive enough to detect the degree of photoresist carbonization (integrated dose monitoring), for example. In the presence of some background gas, $O_2$, $H_2$, and the like, the ion induced luminescence signal can be used to detect the degree of silicon damage through the formation of Si—OH, Si—O or Si—H peaks, which have very high ion induced luminescence signals. For example, Si—O has a strong IIL peak at about 390 nm, and Si—OH a strong peak at approximately 460 nm.

Another aspect of the present invention is that the ion induced luminescence signal can be used for pressure compensation and/or to determine outgassing effects. In most cases at least fifty percent of the wafer surface area is coated with photoresist, an organic material, during a given implantation process. Most organic materials have a high ion induced luminescence yield, however the ion induced luminescence yield of most organic materials degrades as more dose is delivered to the substrate surface and this degradation may be an indicator of the total integrated dose. By monitoring this signal, one may feed-back the integrated dose signal to the control electronics to compensate for previous dose non-uniformities. By comparing characteristic peak ratios of undamaged photoresist to damaged photoresist, for example, accurate measurements of the total dose variations can be determined. The IIL information can be used to monitor, detect and fix "real time implant errors", such as glitches, during a re-paint condition, for example.

Another aspect of the present invention is that the signal can have a faster time response, than current monitoring systems, since the ion induced luminescence response time is of the order of $10^{-12}$-$10^{-8}$ seconds for most inorganic materials and of the order of $10^{-9}$-$10^{-7}$ seconds for organic materials. High gain, low-noise photodetectors, such as photomultipliers are readily available so that accurate and fast detection times at low beam currents can be achieved. As discussed supra, the time response for Faraday cups is in the millisecond range and therefore the response time for the present invention can be orders of magnitude faster than current approaches.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

Figure 1:
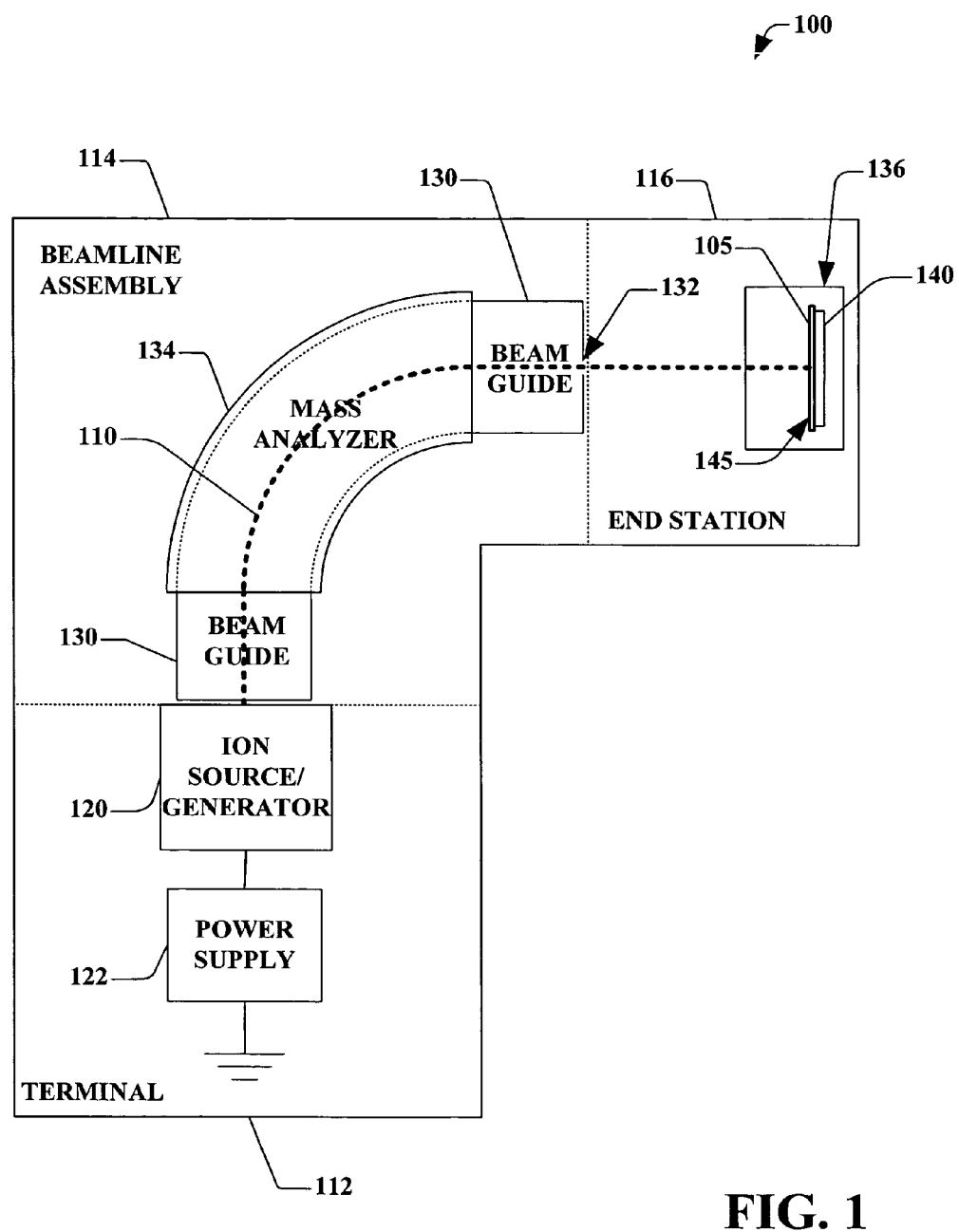
FIG. 1 is a plan view of an exemplary ion implantation system according to one aspect of the present invention.

The present invention is directed generally towards a system and method for employing ion induced luminescence when manufacturing or processing semiconductors using an ion implantation system. More particularly, the system and method provides an optimized approach based on one or more performance criteria associated with the ion source implantation system. Accordingly, the present invention will now be described with reference to the drawings, wherein like reference numerals are used to refer to like elements throughout. It should be understood that the description of these aspects are merely illustrative and that they should not be taken in a limiting sense. In the following description, for purposes of explanation, numerous specific details are set forth in order to provide a thorough understanding of the present invention. It will be evident to one of ordinary skill in the art, however, that the present invention may be practiced without these specific details.

Referring now to the figures, in accordance with one exemplary aspect of the present invention, FIG. 1 illustrates an exemplary hybrid-scan, single-substrate ion implantation system 100, wherein the system can be operable to scan an ion beam 110 in a first scan direction and scan the substrate 105 in the orthogonal slow scan direction. As stated above, various aspects of the present invention may be implemented in association with any type of ion implantation apparatus, including, but not limited, to the exemplary system 100 of FIG. 1. The exemplary ion implantation system 100 comprises a terminal 112, a beamline assembly 114, and an end station 116 that forms a process chamber in which the ion beam 110 is directed to a workpiece location. An ion source 120 in the terminal 112 is powered by a power supply 122 to provide an extracted ion beam 110 to the beamline assembly 114, wherein the source 120 comprises one or more extraction electrodes (not shown) to extract ions from the source chamber and thereby to direct the extracted ion beam 110 toward the beamline assembly 114.

The beamline assembly 114, for example, can comprise a beamguide 130 having an entrance near the source 120 and an exit with a resolving aperture 132, as well as a mass analyzer 134 that receives the extracted ion beam 110 and creates a dipole magnetic field to pass only ions of appropriate momentum or range thereof (e.g., a mass analyzed ion beam 110 having ions of a desired mass range) through the resolving aperture 132. The scan system scans the ion beam 110 in the first scan direction, for example and may be an electrostatic system, a magnetic system, a mechanical system, and the like. The beam 110 then passes through a parallelizing system to make the beams at all scan angles parallel. The beam 110 can then be delivered to the substrate 105 on a workpiece scanning system 136 associated with the end station 116. Various beam forming and shaping structures (not shown) associated with the beamline assembly 114 may be further provided, for example to maintain and bound the ion beam 110 when the ion beam 110 is transported along a beam path to the substrate 105 supported on the workpiece scanning system 136.

The end station 116 illustrated in FIG. 1, for example, can be a "serial" type end station that provides an evacuated process chamber in which the single substrate 105 (e.g., a semiconductor wafer, display panel, other workpiece, etc.) is supported along the beam path for implantation with ions. It should be noted, however, that batch or other type end stations may alternatively be employed, and fall within the scope of the present invention. In an alternative aspect of the present invention, the system 100 comprises a workpiece scanning system capable of scanning in both the fast and generally orthogonal slow scan directions. In yet another aspect of the present invention, the system 100 can comprise a system wherein both ion beam axes are either electrically or magnetically scanned or a combination thereof. Accordingly, all such scanned or non-scanned ion beams 110 are contemplated as falling within the scope of the present invention.

Figure 2:
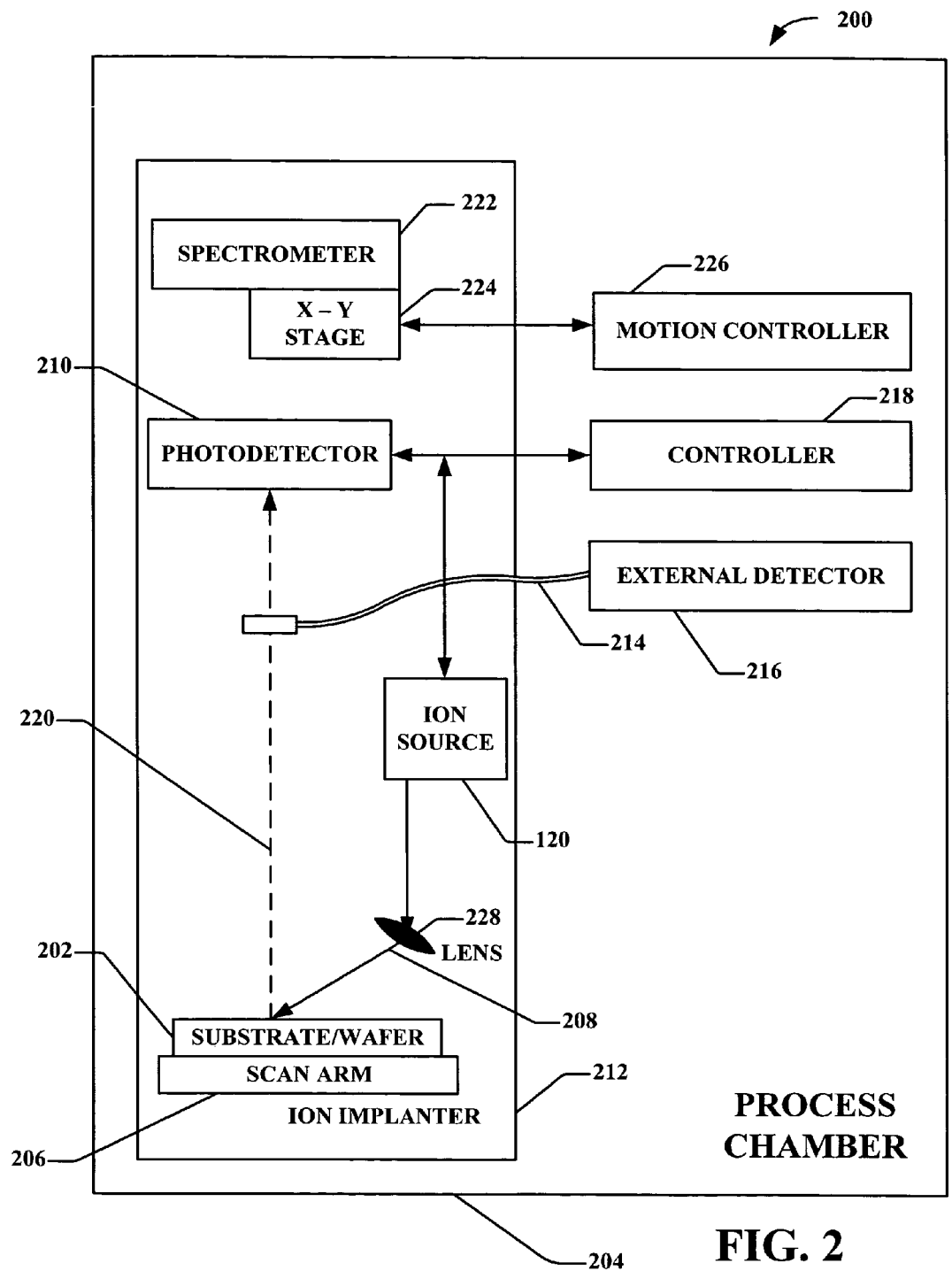
FIG. 2 is a block diagram of an exemplary ion implantation system according to another aspect of the present invention.

According to another aspect of the present invention, FIG. 2 illustrates a schematic block diagram of an ion implanter that employs ion induced luminescence as feedback control. The illustration is of the ion beam implantation system wherein the ion beam is scanned in the first scan direction (e.g., horizontally) and the workpiece 202 moves in the slow scan direction (e.g., vertically), both relative to the fixed process chamber 204. The workpiece scanning system 200, for example, comprises a movable stage 206 whereon the substrate 202 resides, wherein the ion beam 208 is operable to scan the substrate 202 along a first scan direction axis through a lens 228, for example and can translate the wafer 202 along a generally orthogonal slow scan axis with respect to the ion beam 208. Given speeds of the beam along the first scan speed axis (also referred to as, for example, the "fast scan speed direction") can be, for example, significantly faster than a speed of the substrate along, for example, the slow scan axis (also referred to as the "slow scan direction"). Thus the fast scan lines can appear horizontal. As the slow scan speed increases relative to the fast scan speed, the fast scan lines can "tilt". For convenience, the speeds of the beam along the fast scan speed axis will be referred to as either "fast scan speed" and the speed of the substrate along the slow scan axis will be referred to as "slow scan speed". However, it should be apparent to one of ordinary skill in the art that the speeds in either axis can be adjusted to a wide range of values and the fast scan speed in this example could be utilized as a slow speed scan axis, for example.

FIG. 2 illustrates a wide optical bandwidth photodetector 210 placed into an ion implanter 212, looking directly at a wafer 202 surface. The photodetector 210 can be placed directly into the ion implantation chamber 212, or the photodetector 210 can be, for example an optical fiber or array of fibers 214 as needed for imaging the beam employed to conduct ion induced luminescence photons 220 out of the ion implantation chamber 212 to an external detector 216. The optical ion induced luminescence emission intensity is a function of the ionic beam current density. The intensity of the optical signal can be monitored as a beam 208 scans the wafer 202 and signals from the detector 210 can be used to provide feedback to scanning or beam control 218 electronics to detect: beam glitches, beam current fluctuations, beam instabilities, surface element identification, beam profile and the like. This information can them be used to: repaint or touchup ion implantation in those regions of the wafer 202 that experienced lower total doses, vary the implant dose in real-time, and the like. The ion induced luminescence rise time is of the order of $10^{-12}$-$10^{-8}$ seconds for most inorganic materials and of the order of $10^{-9}$-$10^{-7}$ seconds for organic materials.

Additionally a known scintillator material could be placed on the scan arm 206, on the outside edge of the wafer 202, and the like. The scintillator material can be used to calibrate the wafer ion induced luminescence signal 220 to the known scintillator material reference signal during the scan. Known scintillator materials comprise silicon dioxide, doped silicon dioxide, aluminum oxide, barium, lead, bismuth, lead fluoride, barium fluoride, cesium halides, lithium fluoride, bismuth germinate, organic scintillators containing one or more unsaturated carbon bonds, organic scintillators containing one or more chromophores, polyvinyl toluene, polyamide, para-terphenyl, and the like.

In yet another exemplary embodiment of the present invention, a spectrometer 222 can be used in combination with the photodetector 210, with or without the addition of a small quantity of reactive gas to the implanter ($H_2$, $O_2$, etc.). The spectrometer 222, mounted on an x-y stage 224 controlled by a motion controller 226, can allow detection of signals at specific wavelengths, for example. For example, the detector 210 can be set to a wavelength of about 460 nanometers, a characteristic emission peak for Si—OH. It is expected that Si—OH would be formed during the ion implantation process and could act as an on-wafer total dose detector. By monitoring the Si—OH peak during implantation, corrections or modifications for total dose can be made, for example. In another approach the relative peak heights of 390 nm—characteristic of Si—O can be monitored relative to the 460 nm peak characteristic of Si—OH. By comparing the ratio of these two peaks the effect of ion beam current fluctuations can be reduced.

Figure 2A:
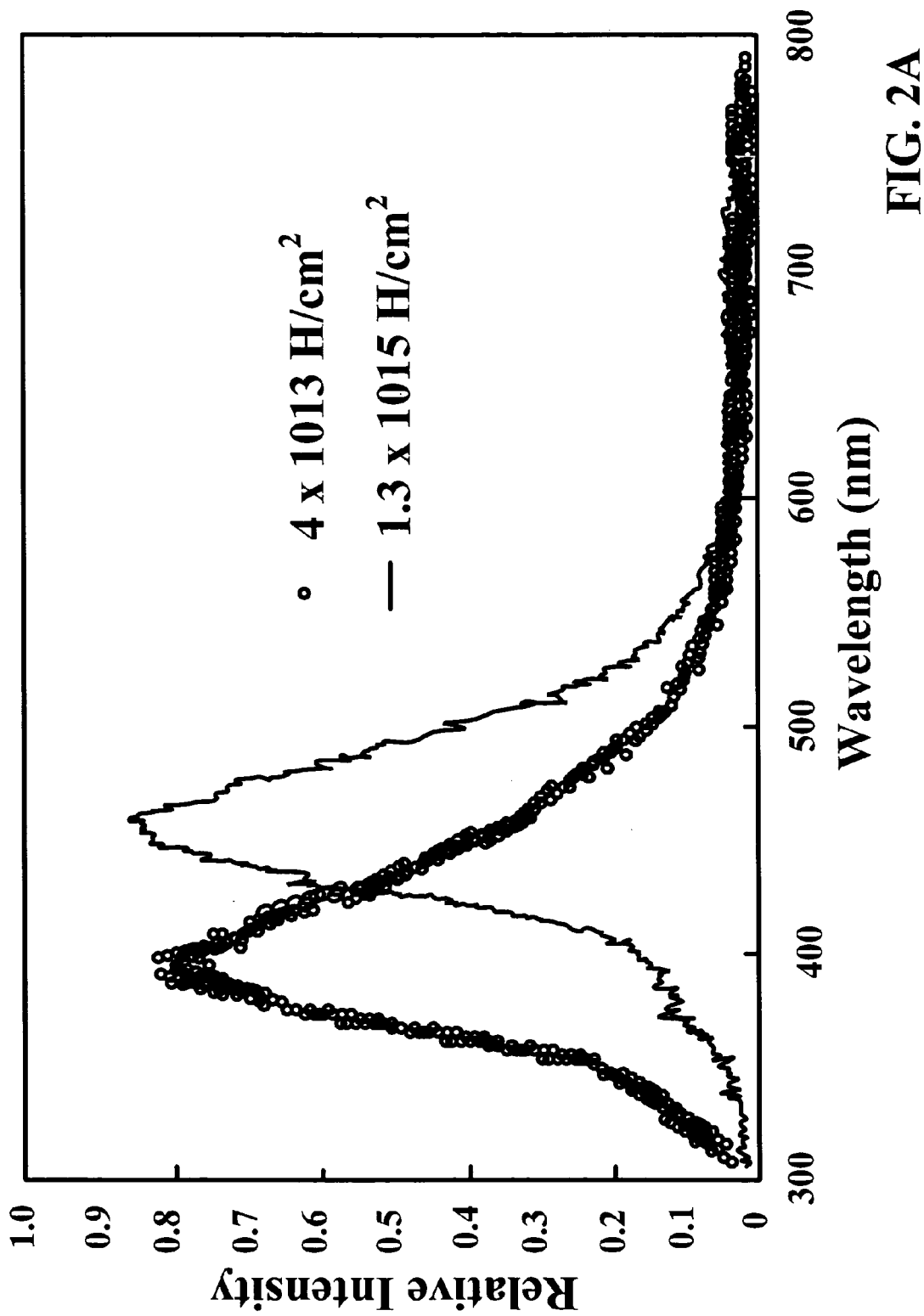
FIG. 2A is a graph IIL signal relative intensity vs. wavelength for SiO₂ material subjected to hydrogen ion bombardment. As the sample is bombarded the Si—O peak at 390 nm is slowly degraded and replaced by the Si—OH peak at 460 nm, in accordance with an aspect of the invention.
Figure 2B:
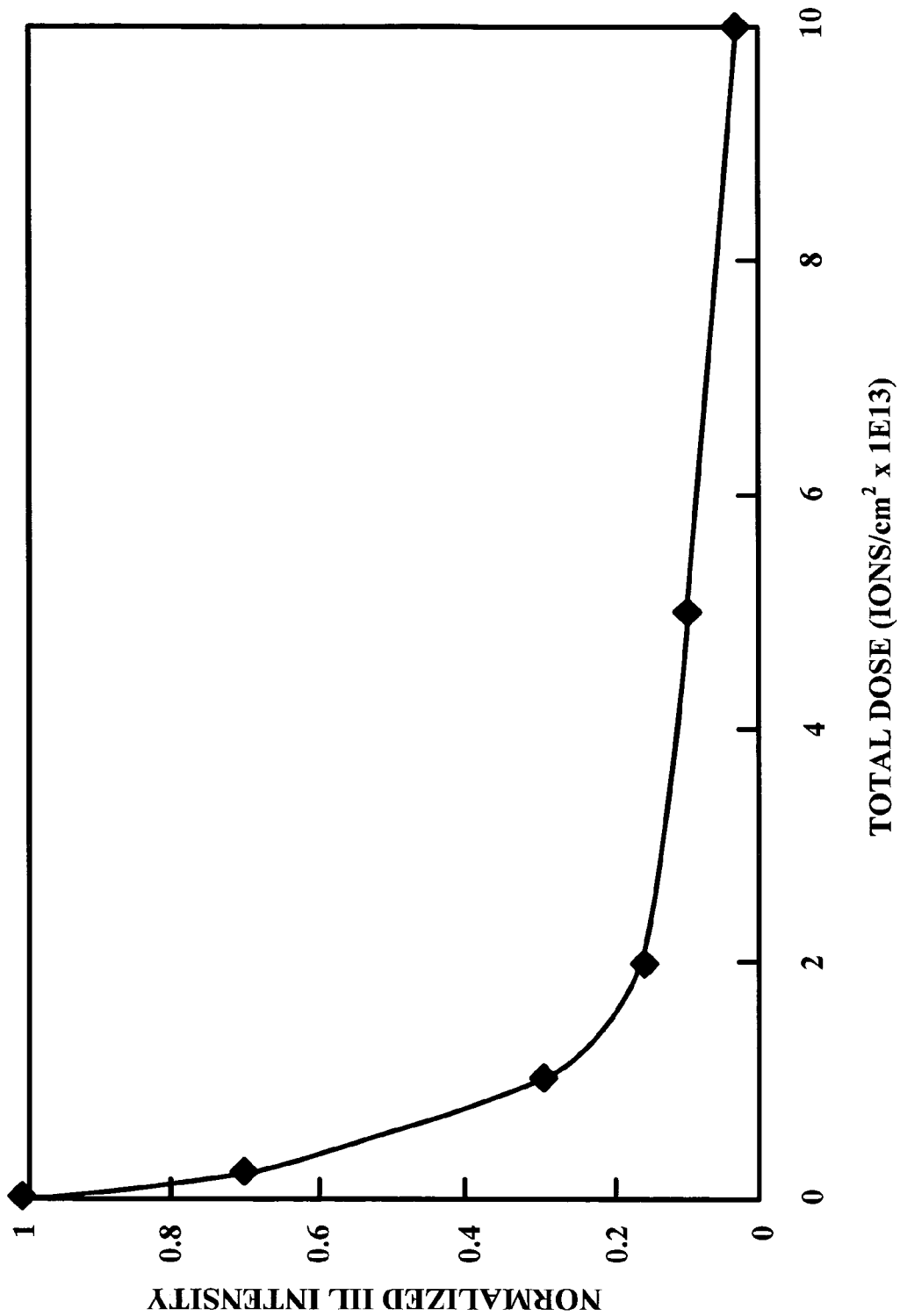
FIG. 2B is an IIL signal normalized intensity from an organic polymer vs. total dosage. The IIL signal decreases with increasing dose as the polymer is ion damaged, according to yet another aspect of the invention.

FIG. 2A represents the IIL signal from an $SiO_2$ sample exposed to an ion beam, for example. As the total ion dose increases the 460 nm peak increases as the 390 nm peak decreases. This can also allow for corrections of macro-level non-uniformities due to source glitches during a re-paint process, for example. Alternatively, for example, the spectrometer 222 could be set to monitor C—C or C═C peaks in the photoresist, as this would also yield the degree of resist carbonization, again as an integrated, total dose detector. The comparisons can be carried out within a microprocessor that is part of the overall system. It can be expected that ion damage could also modify the spectral response of the substrate 202 and that this could also be used as a total dose monitor to ensure the proper dosing of the wafer 202. As shown in FIG. 2B, for example, the IIL signal intensity from an organic material like a photoresist decreases with increasing total ion dose, and by monitoring the IIL intensity the system can measure the total integrated dose. Accordingly, all such monitoring of materials, as known by one of ordinary skill in the art, is contemplated as falling within the scope of the present invention.

Figure 3:
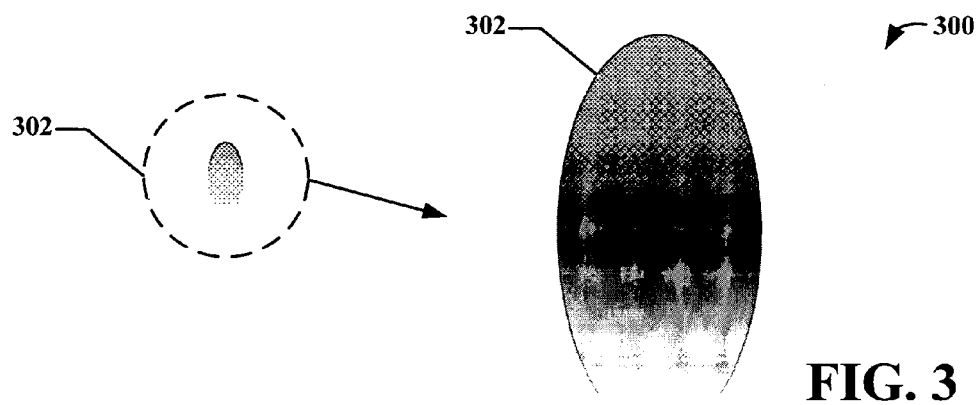
FIG. 3 is an exemplary plan view of ion beam dosing according to another exemplary aspect of the invention.

Referring to FIG. 3, in yet another exemplary embodiment of the present invention, an optical detector can be employed as an imaging detector. For example, a complimentary metal oxide semiconductor (CMOS) imaging detector, a charged coupled device (CCD) array, and the like, can be used as an image sensor that can detect, image and store an IIL beam 302 detected on the wafer. CMOS detectors are popular in the low-cost imaging market, for example, whereas charge coupled device arrays tend more toward high-performance imaging. In a typical CCD array the image can be projected, for example, onto a linked or coupled pixel array, that can cause each pixel to build up an electrical charge that is proportional to the light intensity measured or detected at a specific location. A two-dimensional (2D) CCD array retains the entire image as utilized in, for example digital cameras, digital video recorders, telescopes, night vision devices, and the like. Once the array has detected the image, a control circuit causes each pixel to transfer its contents to its adjacent pixel. The last pixel in the array can off-load its charge into an amplifier(s) that converts the charge into a voltage. By repeating this process, the control circuit can convert the entire contents of the array to a varying voltage, which it samples, digitizes and stores in memory as an image, for example. Stored images can then be transferred to a printer, a video display or to a storage device, for example.

The digital image of the beam 302 yields information as to the beam size, beam shape, beam current density, and the like. Such information can be used in beam setup or beam tuning to achieve a desirable beam profile, a desired beam centering or positioning, as well as controlling the beam current density over the profile. The two-dimensional optical intensity "image" of the beam yields information as to the beam uniformity, this information can be used to adjust and correct any beam asymmetries, coma distortions, and the like that are representative of beam hot-spots that would arise in an implant non-uniformity.

Figure 4:
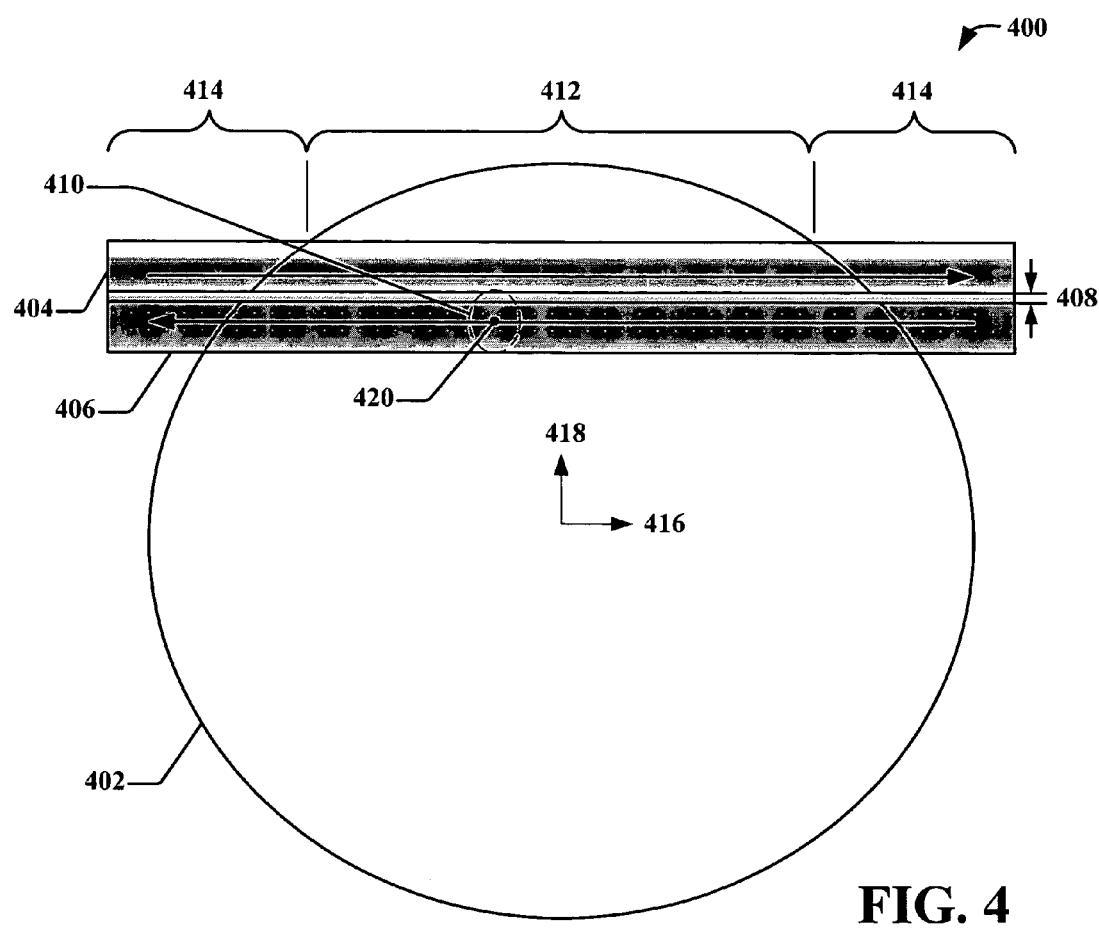
FIG. 4 is a top view of an ion implantation system beam in accordance with another exemplary aspect of the present invention.
Figure 6:
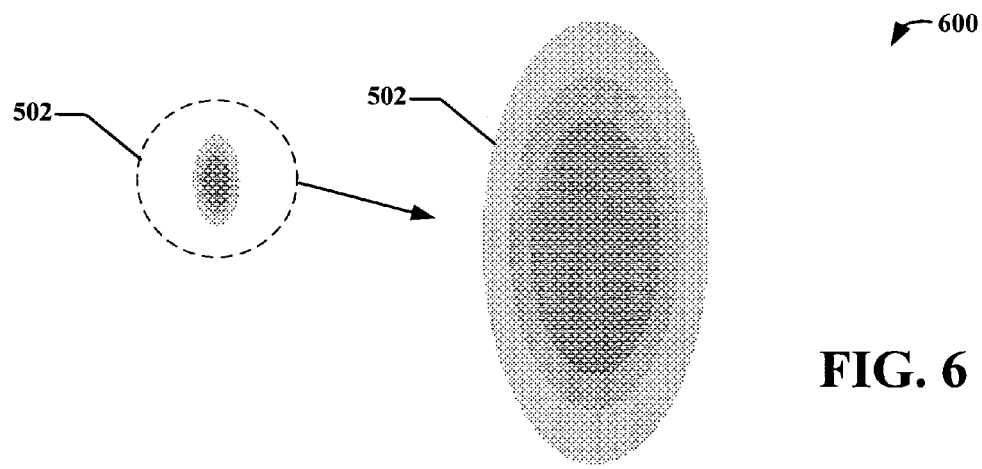
FIG. 6 is a top view of an ion beam per another exemplary ion source implantation system according to another aspect of the invention.

FIG. 4 illustrates one or more aspects of the present invention, induced luminescence provides feedback control for ion implantation and thus "increased across wafer uniformity" can be attained by selectively maneuvering a workpiece or wafer 402 back and forth through a substantially stationary ion beam 410 at the location 420 in a controlled manner. Such implantation is advantageously a function of the location of the workpiece relative to the ion beam. Scanning the workpiece and/or the beam in an optimized manner can improve uniformity and throughput by monitoring the beam profile and adjusting the scan parameters to get adequate but not excessive overlap. An advantage of the present invention may be appreciated by referring to the differences illustrated between FIG. 4 and FIG. 6 (to be explained infra), for example. In FIG. 4, the workpiece 402 is depicted with an exemplary first scan 404 and second scan 406 overlying the wafer 402 at location 420.

The overall scan pattern can be created and stored in a microprocessor or CPU memory by scanning the ion beam 410 back and forth along a horizontal or "X" scan path 416, for example, where the horizontal scan path 416 corresponds to both a scan portion on workpiece 412 plus an overscan 414 on both ends of the wafer 402, wherein the ion beam is scanned is off of the wafer 402. In other words, the overscan 414 corresponds to when the beam 410 is scanned past the workpiece 402 and therefore no longer impinges on the workpiece 402. The workpiece and/or beam can also be moved along a vertical or "Y" scan path 418 as the beam oscillates along the first scan path 416. It is to be appreciated that an overall scan pattern selected can be independent of the size and/or shape of the workpiece 402 in that only the widest portion of the workpiece 402 is considered so that the overall scan pattern is large enough to cover this widest portion of the workpiece 402. As such, substantial overscan can exist within the scan pattern, particularly in areas other than at the widest portion of the workpiece 402. At those locations where the beam is scanned past the wafer 402 the beam can be detected by a Faraday cup, for example.

One or more aspects of the present invention facilitate controlling the scanning of the workpiece 402 with respect to a substantially fixed or stationary ion beam 410 such that that an overlap 408 developed thereby can be determined by the ion luminescence. In the illustrated example, the workpiece can be indexed one increment along a second axis 418 between respective oscillations, 404 and 406, along a first scan path 416. As such, the overlap 408 can be controlled in accordance with one or more aspects of the present invention by analyzing the beam pattern 302, as discussed supra. Adjusting the ion implantation in this manner can result in more uniform distribution of ions than is typically obtained with current systems. It is to be appreciated that many combinations of scanning exist; wherein the workpiece and/or the beam is scanned and all of those approaches are contemplated in the present invention.

Figure 5:
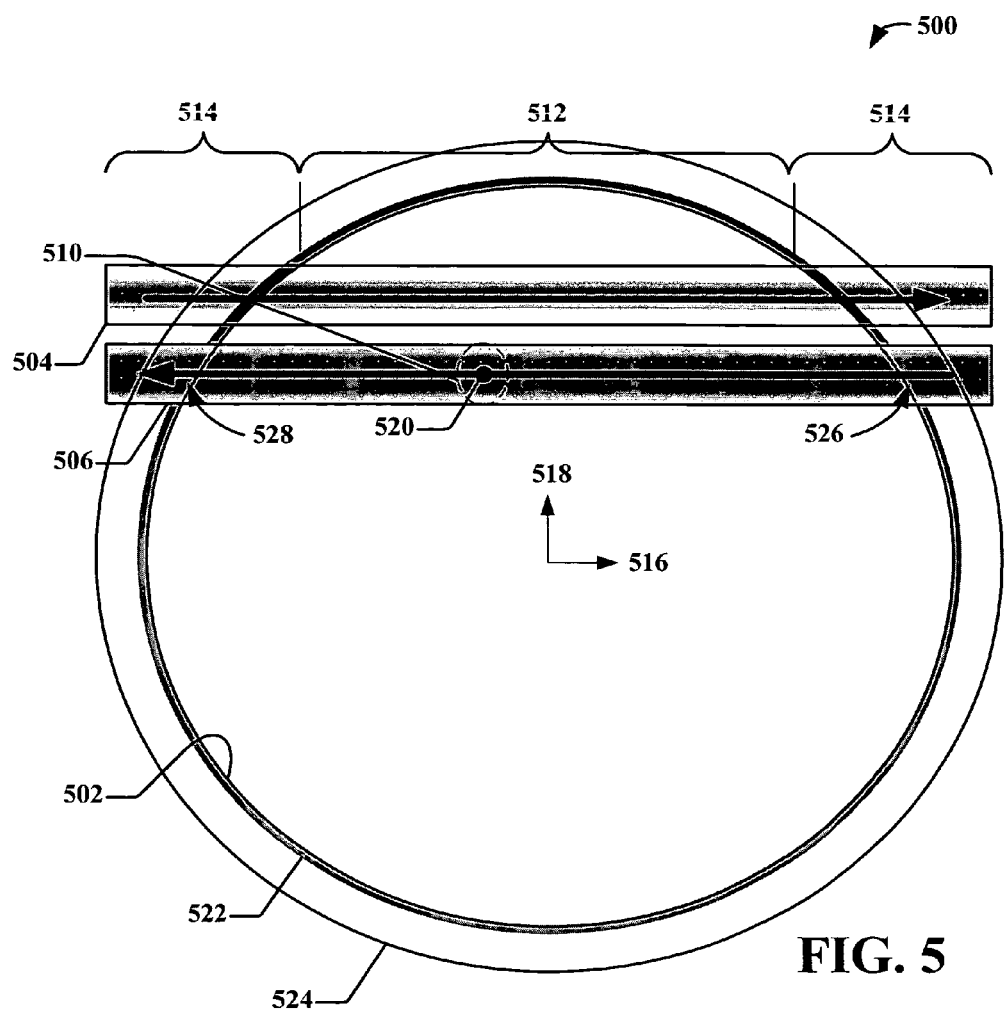
FIG. 5 is a top plan view of an ion implantation system beam scan per another exemplary ion implantation system according to yet another exemplary aspect of the invention.

FIG. 5 illustrates yet one or more aspects of the present invention. The wafer uniformity can be ensured while mechanically maneuvering a workpiece or wafer 502 back and forth through a substantially stationary ion beam 510 at the location 520. Scanning the workpiece 502 in an optimized manner improves ion implantation uniformity by ensuring the indexing, speed, and the like of the wafer platform 524 mounted on a scan arm (not shown) with each scan of the wafer 502 through the stationary ion beam 510. In FIG. 5, the workpiece 502 is shown with the wafer scanned 504 by moving the platform 524 from right to left through the stationary beam 502, along the axis 516. The scan 504 initially begins off of the wafer 502 and proceeds to on the wafer and off of the wafer at, for example. The wafer platform is then indexed along the axis 518 moving up vertically a predetermined distance. The wafer platform 524 can then be scanned or moved along axis 516, from left to right.

The beam pattern 510 at a given location 520 can be utilized and compared to patterns stored in a microprocessor or a CPU, for example. The beam pattern 510 shown in FIG. 6, for example can indicate that the ion beam scans are not overlapping and therefore there can be areas of the wafer 502 that are not properly implanted. Using these data scan parameters, for example, the ion beam travel can be adjusted to maintain a more optimum step size.

One or more aspects of the present invention facilitate controlling the scanning of the workpiece 502 with respect to a known scintillation material 522 deposited on the scan platform 524, the outer edge of the wafer 502, and the like. In the illustrated example, the workpiece 502 has been indexed one increment along a second or slow scan path 118 between respective oscillations, 504 and 506, along the first scan path 114. During the platform 524 scan 506, for example the photodetector can detect the scintillation material 522 at the right edge of the wafer 526 and again at the left edge of the wafer 526. The scintillation material 522 being of known material has a characteristic wavelength and can be utilized to calibrate the ion implantation system. In addition, the system could use the scintillation material 522 data to determine when the ion beam is both on and off of the substrate 502. Adjusting the ion implantation in this manner can result in more uniform distribution of ions than is typically obtained with current systems.

Figure 7:
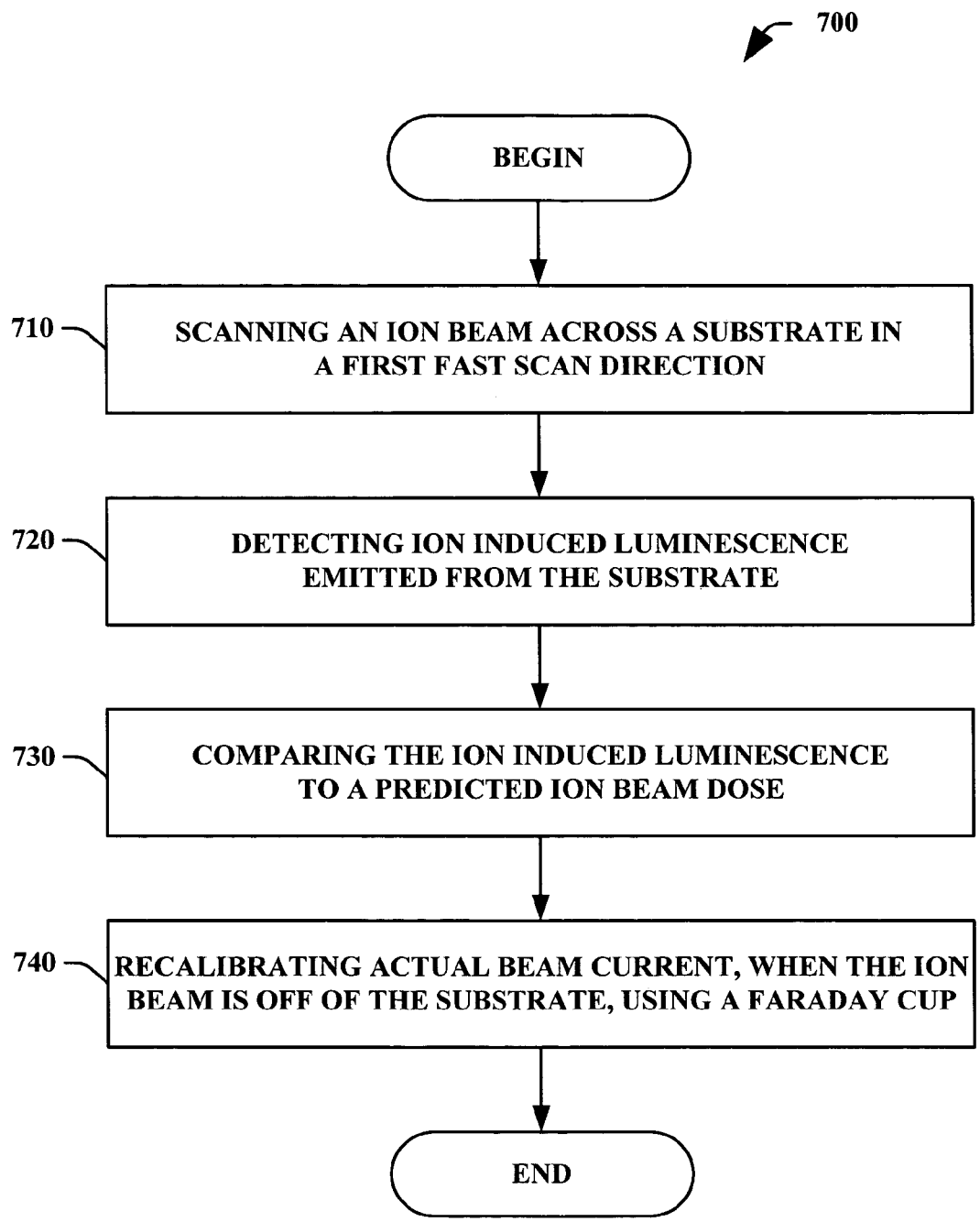
FIG. 7 is a block diagram of an exemplary method for optimizing an ion beam of an ion implantation system according to another exemplary aspect of the invention.

FIG. 7 is a flow diagram illustrating an example of a methodology for utilizing ion induced luminescence signal to compensate for pressure and/or outgassing effects, in accordance with an aspect of the present invention. While, for purposes of simplicity of explanation, the methodology of FIG. 7 is shown and described as a series of steps, it is to be understood and appreciated that the present invention is not limited to the order of steps, as some steps may, in accordance with the present invention, occur in different orders and/or concurrently with other steps from that shown and described herein. Moreover, not all illustrated steps may be required to implement a methodology in accordance with an aspect of the present invention.

Referring to FIG. 7, the illustrated methodology begins at 710, in which an ion beam can be scanned across the wafer in a fast scan direction, for example. The ion beam may be a positively or negatively charged beam. For sake of brevity, the following methodology will be described only with respect to a positive ion beam.

The ion induced luminescence emanating from the wafer when struck with the ion beam can be detected at 720 by a photodetector and/or a spectrometer, for example. The photodetector, for example can comprise a fiber optic, a photomultiplier, a wide optical bandwidth photodetector, an infrared range photodetector, a CCD array, a complimentary metal oxide semiconductor imaging detector an ultraviolet range photodetector, a visible range photodetector, a photodiode, a metal semiconductor metal semiconductor, a photoresistor, a phototransistor, and the like.

A microprocessor and/or CPU, for example can be utilized at 730 to compare the actual ion induced luminescence to a predicted ion beam signal. In addition the system could look at the emission characteristics (e.g., wavelength, temperature of wafer, etc.) to determine if a glitch has occurred on the wafer, for example. The actual time that the glitch occurred can be determined in the sub-microsecond range, for example, as opposed to current systems which measure in tens of milliseconds.

At 740, when the beam moves off the wafer, the beam can be recalibrating by comparing the IIL beam current to the beam current determined using a Faraday cup, for example. In this manner the system can be adjusted to compensate for pressure or outgassing effects.

Figure 8:
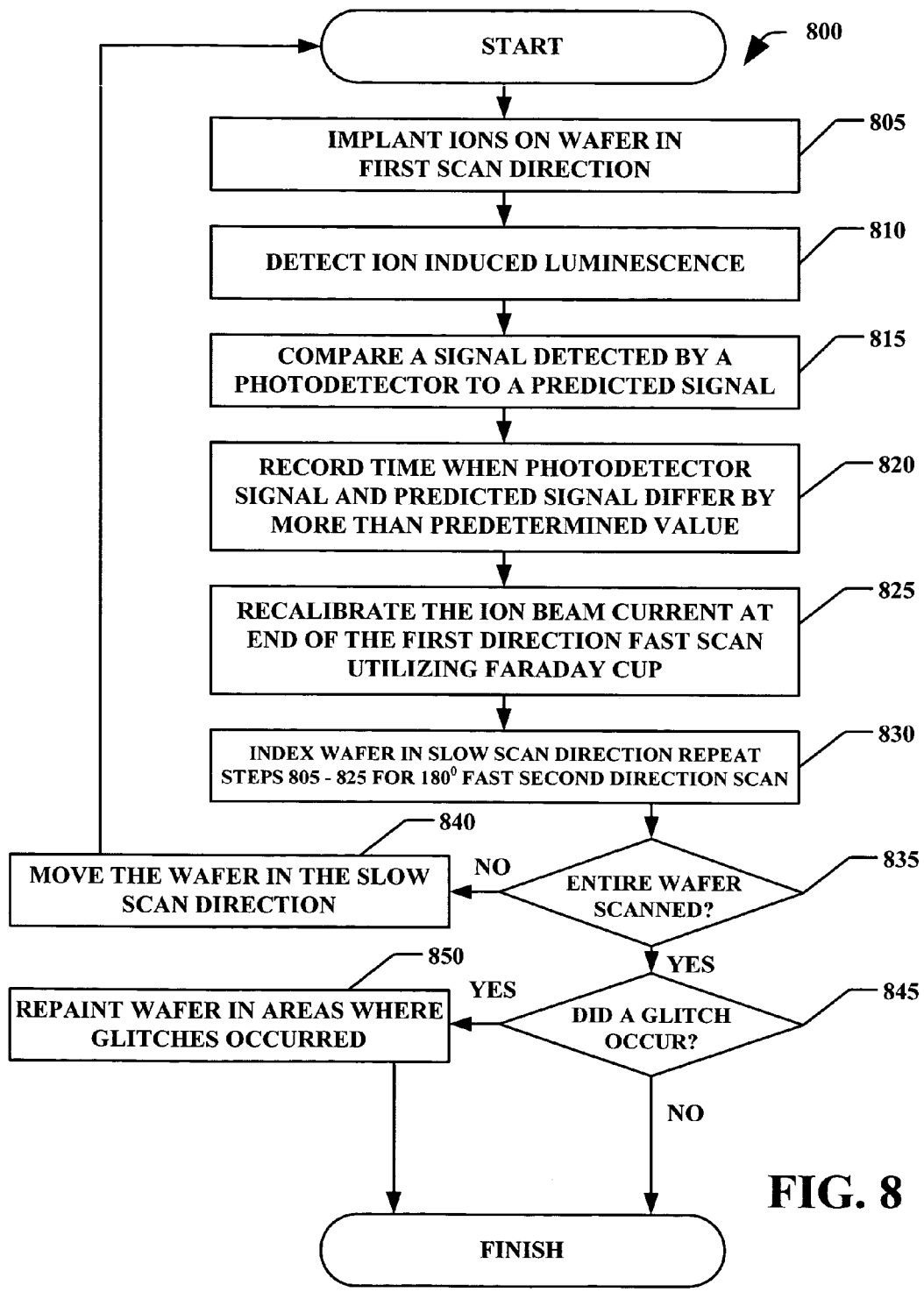
FIG. 8 is a schematic block diagram of an exemplary method for optimizing a scanning system according to yet another aspect of the present invention.

FIG. 8 is a flow diagram illustrating a method 800 mitigating glitches occurring during ion implantation by monitoring ion induced luminescence near a surface of the target wafer or substrate in accordance with an aspect of the present invention. The method 800 can be employed in single and/or batch ion implantation systems, for example.

It is appreciated that the method 800, as well as variations thereof, can be further appreciated with reference to other figures of the present invention. Additionally, the method 800 and description thereof can also be employed to facilitate a better understanding of other aspects of the invention described above.

While, for purposes of simplicity of explanation, the method 800 is depicted and described as executing serially, it is to be understood and appreciated that the present invention is not limited by the illustrated order, as some aspects could, in accordance with the present invention, occur in different orders and/or concurrently with other aspects from that depicted and described herein. Moreover, not all illustrated features may be required to implement a methodology in accordance with an aspect the present invention.

The method 800 begins at block 805 wherein an ion beam is provided. The ion beam can be provided, typically as part of an ion implantation system comprising an ion source, mass analyzer, and a beam line assembly. The ion beam undesirably can comprise contaminants, such as carbon contaminants, that could damage and/or alter a target device. These contaminants can be detected with the present invention, wherein they are not detected with a typical Faraday cup system. The ion beam comprises one or more selected dopants at a selected energy with a selected beam current. The ions can be implanted by scanning the beam across the wafer in a first fast scan direction.

The ion induced luminescence can be detected at block 810 according to process characteristics, such as a given time interval, continuously, and the like. For example, the ion induced luminescence comprising wavelengths of light can be detected continuously in the first fast scan direction. The detector is selected to obtain a predetermined response time within the process chamber and the detected signal can be compared to a predicted signal, at 815, for example. The predicted signal can be based on anticipated molecular bonds for the given wafer, the ion dosage utilized, and the like.

At block 820 a controller and/or microprocessor can record the time of occurrence when the actual photodetector signal and the anticipated or predicted signal differ by more than a predetermined value. The occurrence of an unexpected signal can be due to a glitch, contaminants on the wafer, contaminants within the chamber being released during the implant process, contaminated gas sources, and the like. The system can determine what contaminants are present based upon the wavelengths detected by the photodetector, the spectrometer, and the like, for example.

At 825 the ion beam current can be recalibrated utilizing a Faraday cup as the ion beam traverses off of the end of the wafer in the first direction fast scan. At block 830, the beam can be indexing in the generally orthogonal direction and the process 805 through 825 can be repeated for the ion beam scanning in the second fast scan direction.

The method continues at block 835 wherein it can be determined if the entire wafer has been scanned and therefore implanted. If the entire wafer at 835 has not bean scanned the method proceeds to 840, wherein the wafer can be moved in the slow scan direction, for example by one increment. Subsequently, the method proceeds to 805 where the process continues. In another example, at 835 it can be determined that the entire wafer has been scanned or implanted, wherein the method proceeds to 845. At 845, a determination can be made as to whether a glitch occurred, and if it has the process continues at block 850, wherein the wafer can be repainted with ions in the areas where glitches occurred, for example. Otherwise the process is complete at 845 or 850.

Although the invention has been shown and described with respect to one or more implementations, equivalent alterations and modifications will occur to others skilled in the art based upon a reading and understanding of this specification and the annexed drawings. The invention includes all such modifications and alterations and is limited only by the scope of the following claims. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

The invention claimed is:

1. An ion implantation system utilizing a detected ion induced luminescence signal from a workpiece as feedback control, comprising:
    a photodetector configured to detect ion induced luminescence from the workpiece and generate a signal associated therewith;
    an ion source generator, wherein the ion source generator is configured to implant the workpiece with ions; and
    a controller is configured to utilize the detected ion induced luminescence signal either on the workpiece or off the workpiece, or both on and off the workpiece, and employ the detected ion induced luminescence signal as feedback to control ion beam parameters associated with the ion source generator.

2. The ion implantation system of claim 1, wherein the photodetector comprises one or more of the following: a fiber optic, array of optical fibers, a photomultiplier, a wide optical bandwidth photodetector, an infrared range photodetector, a CCD array, a complimentary metal oxide semiconductor imaging detector, an ultraviolet range photodetector, a deep ultra-violet photodetector, a visible range photodetector, a photodiode, a metal semiconductor metal semiconductor, a photoresistor and a phototransistor.

3. The ion implantation system of claim 1, wherein the detected ion induced luminescence signal is collected and imaged onto the photodetector by one or more lenses or lens elements.

4. The ion implantation system of claim 2, wherein the controller is further configured to interpret the detected ion induced luminescence signal and generate conclusions associated therewith, wherein the conclusions comprise contaminants on the workpiece, chemical properties of the workpiece, and chemical compositions of the workpiece.

5. The ion implantation system of claim 2, wherein the controller is further configured to identify the detected ion induced luminescence signals at specific wavelengths utilizing one or more of the following: a spectrometer, one or more optical filters, and a grating monochromater.

6. The ion implantation system of claim 2, wherein the controller is further configured to determine at least one or more of the following: too much scan overlap, too little scan overlap and optimum scan overlap based upon the detected ion induced luminescence signals.

7. The ion implantation system of claim 2, wherein the controller is configured to monitor one or more peaks characteristics of the workpiece via the detected ion induced luminescence signals comprising: Si—OH, Si—O, Si—H, unsaturated carbon bonds, chromophores, C—C peaks, C=C peaks, degree of resist carbonization, and degree of Si damage.

8. The ion implantation system of claim 7 wherein the controller is configured to measure the ratio of at least 2 characteristic peaks via detecting the ion induced luminescence signals comprising: Si—OH, Si—O, Si—H, unsaturated carbon bonds, chromophores, C—C peaks, C=C peaks, degree of resist carbonization, and degree of Si damage.

9. The ion implantation system of claim 1, wherein the ion beam parameters comprise: ion beam current, ion beam diameter, ion beam density, two dimensional ion beam profile, ion beam position, and ion beam energy.

10. A device for determining ion implantation of a workpiece, comprising:
an ion beam source configured for ion implanting the workpiece;
a photodetector configured for detecting ion induced luminescence emitted from the workpiece and generating a signal associated therewith; and
a microprocessor and a timing circuit configured for monitoring the signal of the photodetector, adjusting to position of the workpiece and regulating the ion beam source to compensate for pressure and outgassing effects within an ion implanting chamber.

11. The device for determining ion implantation of a workpiece of claim 10, wherein the photodetector further comprises: a fiber optic, a photomultiplier, a wide optical bandwidth photodetector, an infrared range photodetector, a CCD array, an ultraviolet range photodetector, a visible range photodetector, a photodiode, an array of photodiodes, an external detector, a metal semiconductor, a photoresistor and a phototransistor.

12. The device for determining ion implantation of a workpiece of claim 10, further comprising: at least one filter or optical spectrometer, for filtering irradiance of at least one predetermined wavelength band from entering the photodetector.

13. A method for optimizing uniformity of ion implantation of a workpiece, the method comprising:

passing the workpiece through an ion spot beam in a first scan direction and a generally orthogonal second scan direction;
detecting ion induced luminescence emitted from the workpiece;
comparing the ion induced luminescence emitted from the workpiece to a measured beam current off of the workpiece or to a measured beam current on an outside edge of the workpiece; and
recalibrating an actual measured beam current on the workpiece away from the outside edge of the workpiece based upon the measured beam current off of the workpiece or the measured beam current on an outside edge of the workpiece or ion induced luminescence signal.

14. The method of claim 13, wherein the ion implantation comprises: a desired ion beam current, an ion beam diameter, a beam scan dwell, a number of passes through the ion beam in a slow scan direction, a desired dosage of ions implanted into the workpiece, and a speed of the workpiece in the slow scan direction.

15. The method of claim 13, further comprising coating the outside edge of the substrate or the substrate platform or both with a known scintillator material configured to calibrate the ion induced luminescence signal to a known scintillator material signal.

16. The method of claim 13, wherein the known scintillator material comprises: barium, lead, bismuth, lead fluoride, barium fluoride, cesium halides, lithium fluoride, bismuth germinate, silicon dioxide, doped silicon dioxide, aluminum oxide, doped aluminum oxide, organic scintillators containing one or more unsaturated carbon bonds, organic scintillators containing one or more chromophores, polyvinyl toluene, polyamide, and para-terphenyl.

17. A method for optimizing uniformity of ion implantation of a workpiece, the method comprising:
translating a workpiece through a stationary ion beam in a first direction;
detecting ion induced luminescence emitted from the workpiece utilizing a photodetector configured to generate a signal associated therewith;
comparing the ion induced luminescence signal to a predicted beam parameter,
recalibrating an actual beam current when the stationary ion beam is off of the workpiece using an beam current measurement device comprising a Faraday detector and an ion beam measurement devise configured to generate an external signal associated therewith; and
translating the workpiece in generally orthogonal second direction.

18. The method of claim 17, wherein an ion beam profile is determined based on one or more of empirical data, or stored sample controller data and a prediction of the ion beam profile based on a process recipe.

19. The method of claim 17, wherein a desired ion implantation maximum non-uniformity is less than 0.1% of one standard deviation across the substrate.

20. An ion implantation system utilizing detected ion induced luminescence signals from a workpiece comprising:
one or more photodetectors configured to detect the ion induced luminescence signals associated therewith, while an ion beam is on the workpiece or off the workpiece or both,
wherein a controller is configured to check for and detect ion beam instability data based upon the ion induced luminescence signal associated therewith; and to use the ion beam instability data to correct for ion implantation dose errors that have occurred during ion beam instabilities.

21. The method of claim 19, wherein once the ion beam instability is detected, the ion beam is turned off, a determined wafer position of the ion beam instability is recorded within a microprocessor, the ion beam is re-stabilized, then the ion beam is returned to the determined wafer position of the ion beam instability, wherein the ion beam is turned on and moved over the workpiece in the areas necessary to correct for the ion beam instability previously detected.

22. A method for determining ion implantation uniformity, the method comprising:
   selecting an ion beam current;
   performing ion implantation of a workpiece in a first direction by moving an ion beam;
   detecting an luminescence emanating from the workpiece utilizing a photodetector;
   comparing the luminescence detected by the photodetector to a predicted luminescence;
   recording a time when the luminescence detected by the photodetector and the predicted luminescence differ by more than a predetermined value;
   recalibrating the ion beam current at an end of the first direction utilizing a first Faraday cup, measurement;
   translating the ion beam a single step in a second generally orthogonal direction;
   performing the ion implantation on the workpiece in a reversed 180° first direction;
   detecting the luminescence emanating from the workpiece;
   comparing the luminescence detected by the photodetector to the predicted luminescence;
   recording a time when the luminescence detected by the photodetector and the predicted luminescence differ by more than the predetermined value;
   recalibrating the ion beam current at the end of the second direction reversed 180° first direction utilizing a second Faraday cup, measurement;
   determining if a potential glitch occurred based upon the luminescence emanating from the workpiece;
   recording time or workpiece position or both during which the potential glitch occurred if the potential glitch took place;
   moving the ion beam the single step in the second generally orthogonal direction;
   determining if the workpiece has been completely implanted; and
   repainting the workpiece positions where the potential glitches occurred, if necessary.

23. The method of claim 22, the luminescence comprises visible light, ultraviolet light and infrared light.

24. The method of claim 22, luminescence emission wavelengths range from about 200 nanometers to 800 nanometers.

25. The method of claim 22, the luminescence wavelengths range from about 200 nanometers to 1 millimeter.

26. The method of claim 22, wherein when the potential glitch is detected, the ion beam current is turned off momentarily and the ion beam current re-stabilized, prior to re-painting the workpiece positions missed during the potential glitch.

27. The method of claim 22, wherein the workpiece is moved or the ion beam is moved or both.

28. A method for determining and controlling the two dimensional ion beam profile comprising:
   positioning an ion beam on a wafer, substrate, workpiece or specially prepared imaging area,
   imaging a resultant ion induced illuminscence signal from said wafer, substrate, workpiece or specially prepared imaging area onto an imaging detector, and
   feeding the resultant ion induced illuminscence signal back into a beam tuning algorithm to correct for one or more of the following: beam profile, beam position, beam shape, and beam current density for each tune cycle.

29. The method of claim 28, further comprising using the imaged ion induced luminescence information to set or control the scan velocities, degree of scan overlap, and over-scan parameters so as to maximize across wafer, substrate, or workpiece uniformity and optimize beam utilization.

30. The method of claim 28 wherein the ion induced luminescence detector is a solid state imaging detector comprising a CCD array and a CMOS imaging detector.

* * * * *